United States Patent [19]

Linden

[11] Patent Number: 4,730,635

[45] Date of Patent: Mar. 15, 1988

[54] VALVE AND METHOD

[75] Inventor: Harry A. Linden, Santa Barbara, Calif.

[73] Assignee: Hall Surgical, Carpinteria, Calif.

[21] Appl. No.: 87,140

[22] Filed: Aug. 19, 1987

[51] Int. Cl.⁴ .................... F16K 31/126; F16L 55/10
[52] U.S. Cl. ......................................... 137/1; 251/5;
                             251/61; 251/61.1; 251/342; 604/247
[58] Field of Search ................... 251/4, 5, 61, 61.1,
                                  251/342, 846; 604/9, 34, 247

[56] References Cited

U.S. PATENT DOCUMENTS

| | | | |
|---|---|---|---|
| 274,447 | 3/1883 | Kennish | 604/247 |
| 2,314,767 | 3/1943 | Burrell | 251/8 |
| 2,518,165 | 8/1950 | Millard | 251/342 |
| 2,706,101 | 4/1955 | Cantor | 251/342 |
| 3,819,151 | 6/1974 | Kish | 251/342 |
| 3,889,675 | 6/1975 | Stewart | 251/342 |
| 3,936,028 | 2/1976 | Norton et al. | 251/5 |
| 4,106,675 | 8/1978 | Taylor | 251/342 |
| 4,195,810 | 4/1980 | Lavin | 251/5 |
| 4,310,140 | 1/1982 | Boomer et al. | 251/5 |
| 4,456,223 | 6/1984 | Ebling | 251/342 |

FOREIGN PATENT DOCUMENTS

| | | | |
|---|---|---|---|
| 0004629 | 1/1980 | Japan | 251/5 |
| 833783 | 4/1960 | United Kingdom | 251/8 |
| 1239275 | 7/1971 | United Kingdom | 251/5 |

Primary Examiner—George L. Walton
Attorney, Agent, or Firm—Stuart E. Krieger

[57] ABSTRACT

The valve includes a housing with inlet and outlet members joined by a resilient flexible valve closure. An annular chamber that does not communicate with the inlet or outlet surrounds the valve closure. When a flow of fluid is desired through the valve closure, a pressurized fluid is introduced into the annular chamber to deform the valve closure enabling the closure to open. Reduction or elimination of the pressure for deforming the valve closure permits the valve closure to assume its normal closed position, thereby permitting a shut off of fluid flow. Variable flow rates can be accomplished by obtaining predetermined deformations of the valve closure corresponding to predetermined levels of the pressurizing fluid which cause such deformation.

17 Claims, 8 Drawing Figures

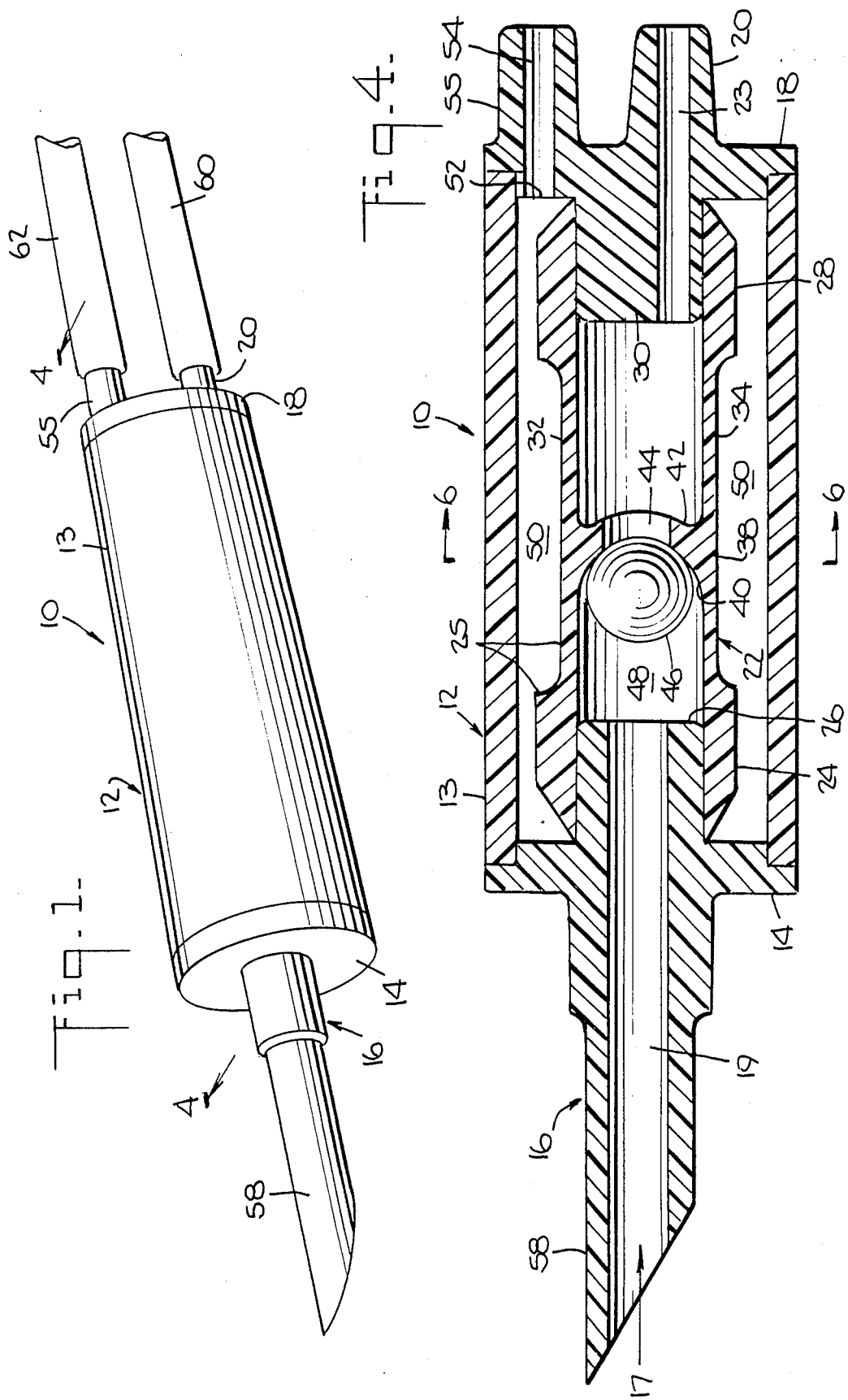

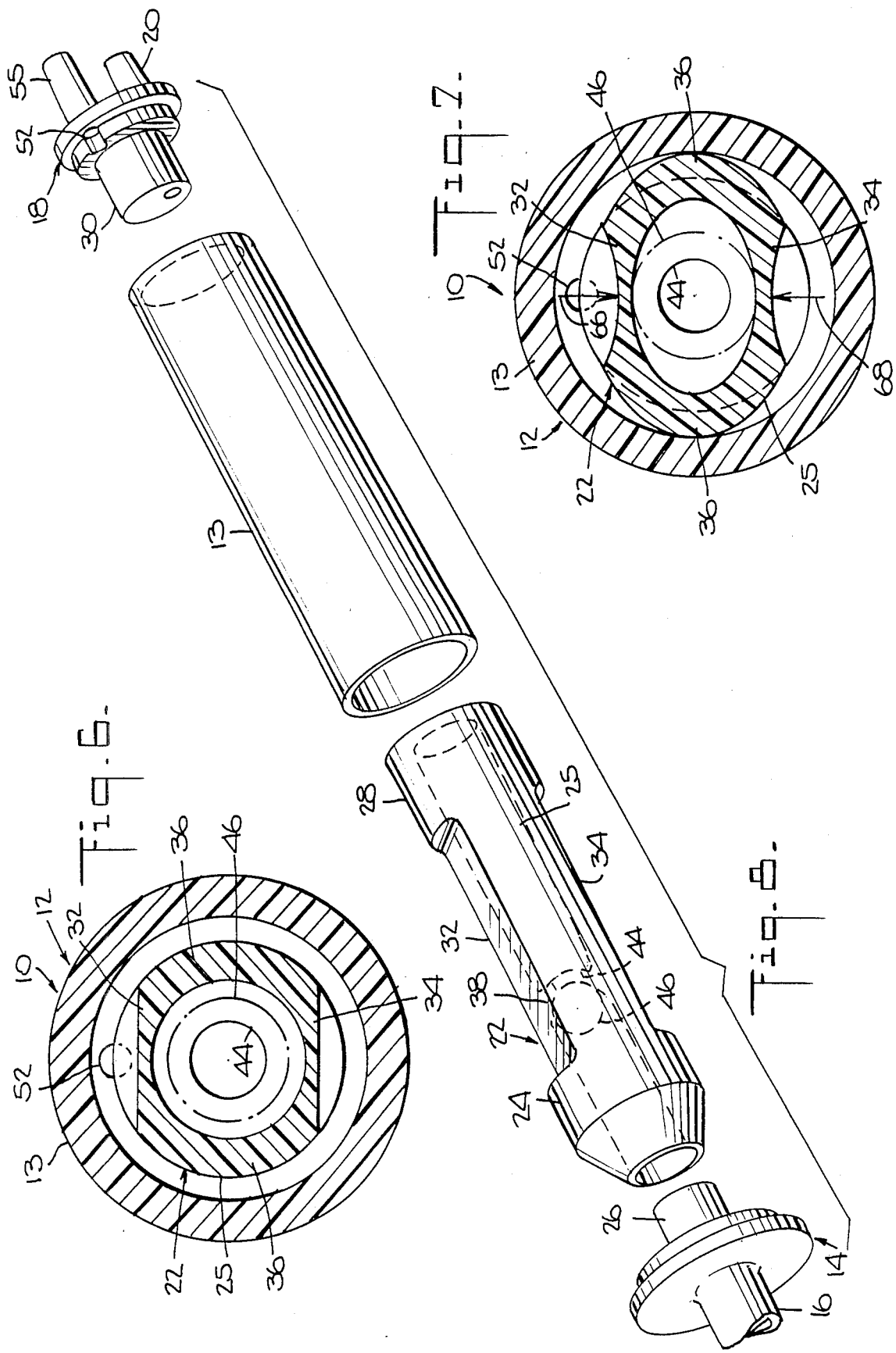

VALVE AND METHOD

BACKGROUND OF THE INVENTION

This invention relates to valves and more particularly to a valve having a valve closure that is remotely operable by pressurized fluid to provide precisely controlled rates of fluid flow, and a nonflow condition.

Valves having flexible, resilient valve closure members that require manual deformation or some form of pressure differential to induce a fluid flow condition are well known.

One known manually deformable valve, as shown in U.S. Pat. No. 3,889,675, includes a bulb-shaped diaphragm with a normally closed slit. Manual depression of the bulb causes the slit to open and permit fluid to pass through the diaphragm. However, it is difficult to precisely control th flow of fluid through the diaphragm because the bulb-shaped diaphragm must be depressed between the fingers an amount that is based upon the operator's judgment.

Other known valves with flexible resilient closure members are automatically maintained in a closed position by imposing fluid pressure on the valve closure at a location that is external to the normal flow of fluid, such as shown in U.S. Pat. No. 4,465,258. Under this arrangement, when fluid flow is desired, pressure on the valve closure is reduced below the level of the fluid flow pressure. However, an unexpected drop in fluid pressure on the valve closure is also likely to cause fluid to flow through the valve when such flow is not desired.

Reductions of pressure in a valve to accomplish fluid flow often require intricate pressure reducing or bypass arrangements such as shown in U.S. Pat. Nos. 4,300,748; 3,936,028 and 2,026,916. Many of these valves do not permit precise control of fluid flow rates and the complexity and cost of such valve structures unduly limits their use.

U.S. Pat. No. 3,371,677 shows a deflectable valve closure having sufficient stiffness to normally stop the flow of fluid. If fluid is not delivered under high pressure, the valve will not open. Thus, high pressures must be imposed on the delivery fluid in order to overcome the valve closure stiffness and obtain fluid flow.

It is thus desirable to provide a valve having a closure arrangement that does not require high delivery pressures to open a valve closure, does not require high external pressures to maintain the valve in a closed condition, and does not require intricate fluid bypass arrangements or pressure reducing operations to cause the valve closure to open.

OBJECTS AND SUMMARY OF THE INVENTION

Among the several objects of the invention may be noted the provision of a novel valve, a novel valve having a resilient deformable valve closure arrangement, a novel valve that can be remotely operated, a novel valve that is actuatable into an open condition by a fluid source having higher pressures than the delivery fluid, a novel valve that employs a fluid separate from the fluid being delivered through the valve to actuate the valve into an open position, a novel valve that is normally maintained in a closed position by the pressure of fluid being delivered through the valve, a novel resilient deformable valve having a spherical valve closure member, and a novel method of remotely controlling the flow of fluid.

Other objects and features of the invention will be in part apparent and in part pointed out hereinafter.

The valve, in accordance with one embodiment of the invention, includes a housing with inlet means for receiving an incoming flow of fluid and outlet means for directing the fluid flow from the housing. A pressure responsive valve means is provided between the inlet and outlet means to control the flow of fluid. The valve means includes a valve closure having a valve opening and a valve seal member for sealing the valve opening.

The valve opening is formed in a resiliently deformable valve seat that is surrounded by a resiliently deformable valve wall. When the valve closure is in a normally closed position, the valve seal member is urged into surface contact with the periphery of the valve opening due to pressure of the delivery fluid against the valve seal member. The valve seal member thus closes the valve opening to prevent fluid flow.

The valve also includes a pressure receiving means cooperable with the valve closure to cause the valve seal member and the valve opening to unseal in response to a predetermined pressurized condition imposed on the resiliently deformable valve wall. The pressure receiving means also has a depressurized condition which does not cause unsealing of the valve seal member and the valve opening.

Preferably, the pressure receiving means includes a chamber that is concentric with the valve wall yet does not communicate with fluid that passes through the valve. Thus, when the pressure receiving means is pressurized, it causes the valve wall and valve seat to resiliently deform thereby causing the valve seal member and the valve opening to unseal. Fluid can then flow through the valve closure.

The amount of fluid flowing through the valve closure varies according to the amount of deformation of the valve seat. The fluid flow rate is thus easily controlled by controlling the pressure level of pressure receiving means to predetermined amounts that correspond to predetermined flow rates.

Depressurization of the pressure receiving means permits the resiliently deformable valve seat to return to a normal nondeformed condition. The valve seal member and the valve opening then engage in a closed position preventing further flow of fluid. The sealing engagement between the valve opening and valve seal member is maintained by the normal pressure of incoming fluid against the valve seal member.

The invention accordingly comprises the constructions and method hereinafter described, the scope of the invention being indicated in the claims.

DESCRIPTION OF THE DRAWINGS

In the accompanying drawings,

FIG. 4 is a sectional view thereof taken on the line 4—4 of FIG. 1, showing the valve in a closed condition;

FIG. 5 is a sectional view similar to FIG. 4 showing the valve in an open condition;

FIG. 6 is a sectional view taken on the line 6—6 of FIG. 4;

FIG. 7 is a sectional view taken on the line 7—7 of FIG. 5; and,

FIG. 8 is a exploded perspective view thereof.

Corresponding reference characters indicate corresponding parts throughout the several views of the drawings.

DETAILED DESCRIPTION OF THE INVENTION

Figure 2:
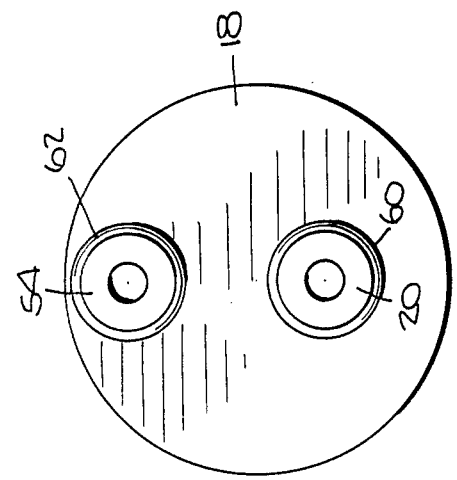
FIG. 2 is an end view of the inlet end thereof.
Figure 3:
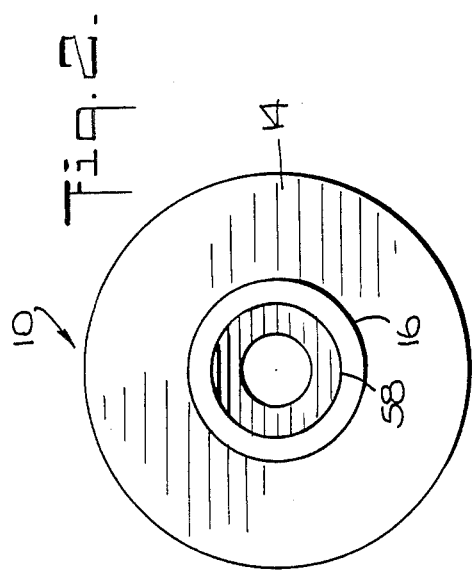
FIG. 3 is an end view of the outlet end thereof.
Figure 1:
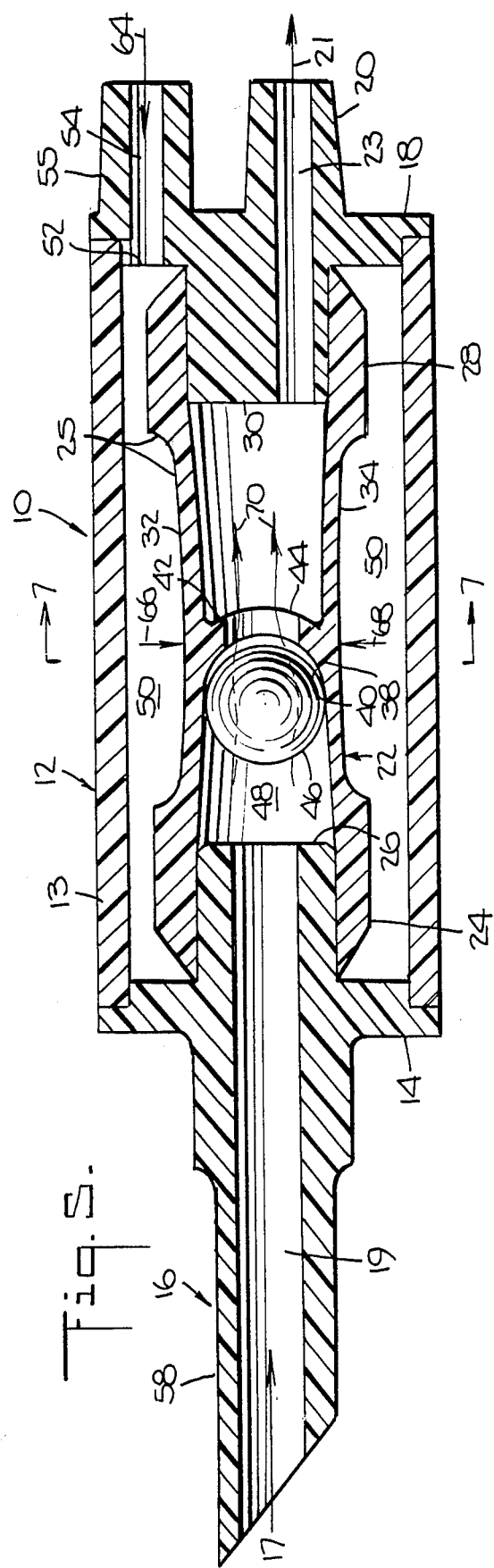
FIG. 1 is a simplified perspective view of a valve incorporating one embodiment of the invention.

A valve incorporating one embodiment of the invention is generally indicated by the reference number 10 in FIG. 1.

The valve 10 comprises a generally cylindrical housing 12 having a cylindrical wall 13. The housing 12 which can be formed of acrylonitrile butadiene styrene (ABS), polyethylene or other similar plastic, has an inlet end 14 with inlet means 16 for receiving incoming fluid represented by the arrow 17, in an inlet duct 19. The housing 12 also includes an outlet end 18 with outlet means 20 for directing the outgoing flow of fluid represented by the arrow 21, through an outlet duct 23 of the outlet means 20.

The housing 12 incorporates an elongated pressure responsive valve means 22 that interconnects the inlet means 16 and the outlet means 20. Preferably the valve means 22 is formed of a resilient, flexible material such as silicone rubber. The valve means 22 includes a generally cylindrical valve wall 25 (FIG. 8) having an end portion 24 that forms a leak-tight seal around an inward extension 26 of the inlet means 16. An opposite end portion 28 of the valve wall 25 forms a leak-tight seal around an inward extension 30 of the outlet means 20.

Referring to FIGS. 4, 7 and 8, the valve wall 25 includes opposite elongated sections 32 and 34 of reduced wall thickness relative to the general wall thickness 36 (FIG. 7) of the valve wall 25. The valve means 22 also includes a valve closure comprising a valve seat 38 having a periphery that laterally joins the reduced wall sections 32 and 34 as well as the nonreduced wall 36. The valve seat 38 has a generally concave contour 40 facing the inward extension 26 and a generally conve contour 42 directed toward the inward extension 30.

A generally circular valve opening 44 is formed in the valve seat 38. A valve seal member 46 in the form of a sphere is disposed in a space 48 defined between the valve seat 38 and the inward extension 26. A portion of the valve seal member 46 seals the periphery of the valve opening 44 when the valve seat is in a normal, nondeformed condition. Thus, when the valve seat 38 is nondeformed, the seal member 46 can close the valve opening 44.

The cylindrical wall 13 of the housing 12 is spaced from the valve wall 25 such that an annular space or chamber 50 is defined between the cylindrical wall 13 and the valve wall 25. The annular chamber 50, which is noncommunicable with the inlet means 16 and the outlet means 20, has a single opening 52 that communicates with a passage 54 in an extension 55 formed on the outlet end 18.

In operation of the valve 10, an inlet tube (not shown) from a fluid supply (not shown) is connected to a reduced end portion 58 of the inlet means 16. An outlet tube 60 (FIG. 1), which leads to a fluid dispensing area (not shown) is connected to the outlet means 20. A pressure tube 62, from a source of pressurized fluid (not shown), is connected to the extension 55.

The incoming fluid 17 normally urges the spherical valve seal member 46 against the valve seat 38 to seal the valve opening 44. Thus under normal conditions there is no flow of fluid through the valve 10, as indicated in FIG. 4.

Fluid is permitted to flow through the valve 10 only when the sealing member 46 and the valve opening 44 are unsealed. Unsealing of the valve closure is accomplished by pressurizing the annular chamber 50 with fluid represented by the arrow 64 (FIG. 5) which flows into the passage 54 for confinement in the chamber 50.

Preferably, the source of the pressurized fluid 64 is different from the source of the fluid 17. Furthermore, the fluid 64 can be a liquid or gas. The source of the pressurized fluid 64 and the controls for regulating the flow of the pressurized fluid 64 can be a substantial distance from the valve 10, if desired, permitting remote operation of the valve 10.

The confinement of pressurized fluid 64 in the annular chamber 50 causes a pressure buildup in the chamber 50 to any selected pressure level. When the pressurized fluid 64 reaches a predetermined level which exceeds, by a predetermined amount, the pressure level of the fluid 17 in the space 48, the valve means 22 will deform as shown in FIG. 5.

Deformation of the valve means 22 will occur in predetermined fashion along the direction indicated by the arrows 66 and 68 in FIGS. 5 and 7. Such deformation is attributable to the location of the reduced wall sections 32 and 34 which constitute the weakest areas in the valve wall 25.

As the valve wall 25 deforms, the valve seat 38 likewise deforms from the normal concave contour of FIG. 4 to the deformed contour of FIG. 5. During such deformation, the spherical sealing member 46 disengages from the valve opening 44, enabling the incoming fluid 17 to flow around the sealing member 46 and through the valve opening 44 in the manner indicated by the arrows 70 of FIG. 5.

The fluid flow 70 is directed toward the outlet duct 23 for outward flow in the direction indicated by the arrow 21. The outward fluid flow 21 is directed by the outlet tube 60 to a desired dispensing area (not shown).

The rate of fluid flow through the valve 10 can be increased or decreased by corresponding increases or decreases in the amount of disengagement between the valve seal member 46 and the valve opening 44. The amount of disengagement is accomplished by increasing or decreasing the deformation of the valve wall 25 and the valve seat 38. Since the amount of deformation of the valve means 22 is dependent upon the pressure levels maintained in the annular chamber 50, the amount of fluid flow through the valve 10 can be precisely controlled by precisely controlling the pressure levels in the annular chamber 50.

Some advantages of the presen invention evident from the foregoing description include a remotely operable valve wherein the rate of fluid flow can be precisely controlled to flow at different predetermined flow rates. When the pressurizing fluid 64 is reduced to a level below that of the incoming fluid 17, the pressure of such incoming fluid 17 causes an immediate seating of the valve seal member 46 against the valve opening 44 thereby immediately shutting off the flow of fluid through the valve. Thus the valve provides an instant reaction to a desired shutoff condition. A further advantage is that the valve 10 is simply constructed of relatively few parts and is easily adaptable to a wide range of use.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A valve comprising
   a. a housing having a first inlet means for receiving flow of a first fluid,
   b. a first outlet means for directing the flow of said first fluid from said housing,
   c. a fluid pressure responsive valve means provided between said first inlet means and said first outlet means, said pressure responsive valve means including a valve opening, a valve seat and a valve seal member for sealing and unsealing said valve opening, said valve means having a closed position wherein said valve seal member seals said valve opening to prevent the flow of said first fluid from said first inlet means to said first outlet means, said valve means having an open condition wherein said valve member does not seal said valve opening thereby permitting said first fluid to flow from said first inlet means through said valve opening to said first outlet means, and
   d. pressure receiving means for receiving a second fluid and cooperable with said valve means for deforming the valve means inwardly and against said valve seal member so as to move said valve seal member away from said valve seat and define a space between said valve seat and said valve seal member and for unsealing the valve opening permitting passage of said first fluid from said inlet to said outlet in response to a predetermined pressurized condition of said pressure receiving means, the pressure receiving means having a depressurized condition which moves the valve means outwardly and the valve member against the valve seat and causes sealing of the valve opening.

2. The valve as claimed in claim 1 wherein said pressure responsive valve means includes a resilient deformable portion communicable with said pressure receiving means, said resilient deformable portion having a normally nondeformed condition corresponding to the depressurized condition of said pressure receiving means, and a deformed condition corresponding to the predetermined pressurized condition of said pressure receiving means.

3. The valve as claimed in claim 2 wherein said deformable portion is formed of a resilient, flexible material.

4. The valve as claimed in claim 1 wherein said valve opening has a circular periphery when said pressure receiving means is in the depressurized condition, and said valve seal member is spherical having a diameter greater than the diameter of said circular opening.

5. The valve as claimed in claim 1 wherein said deformable portion includes an elongated section, said valve seat extending laterally with respect to said elongated section.

6. The valve as claimed in claim 5 wherein said elongated section is of cylindrical shape having a cylindrical wall comprising a portion of reduced wall thickness.

7. The valve as claimed in claim 6 wherein said valve seat is joined to said portion of reduced wall thickness.

8. The valve as claimed in claim 7 including two said portions of reduced wall thickness.

9. The valve as claimed in claim 1 including an annular chamber surrounding said valve means, said annular chamber being noncommunicable with said first inlet means and said first outlet means.

10. The valve as claimed in claim 9 wherein said annular chamber has a single opening.

11. The valve as claimed in claim 1 wherein said valve opening has an inlet side and an outlet side and said valve seal member is disposed at said inlet side.

12. The valve as claimed 1 wherein said valve opening is of a first fixed size when said pressure receiving means is in the depressurized condition.

13. The valve as claimed in claim 1 wherein said valve opening has a circular periphery when said pressure receiving means is in the depressurized condition, and said valve seal member is spherical having a diameter greater than the diameter of said circular periphery.

14. A valve comprising
   a. a housing with first and second chambers having adjacent noncommunicable fluid spaces,
   b. one of said chambers having inlet and outlet ports, a resiliently deformable valve seat having a valve opening disposed betwen said inlet and outlet ports and a moveable valve seal member normally engagable with said valve seat to seal said valve opening, said one chamber being resiliently deformable at said valve seat,
   c. said other chamber having a single opening for introduction of pressurized fluid to deform said one chamber at said valve seat to cause said valve seal member to move away from said valve seat and form a space about said valve seal member and to unseal from said valve opening and to permit fluid to flow from said inlet port through said space and valve opening to said outlet port, depressurization of said other chamber permitting said valve seal member to seal against and close said valve opening.

15. The valve as claimed in claim 14 wherein said first and second chambers are concentric.

16. The valve as claimed in claim 15 wherein said first chamber is surrounded by said second chamber.

17. A method of remotely controlling the flow of fluid comprising
   a. providing a normally closed ball valve closure with a resiliently deformable valve seat having a valve opening, between inlet and outlet fluid ports,
   b. surrounding the deformable valve seat with a pressurizable chamber,
   c. deforming the valve seat by fluidly pressurizing the chamber a predetermined amount with a first fluid to cause the ball valve to move away from said valve opening and causing the valve opening to unseal and permit a second fluid to flow through the valve closure,
   d. depressurizing the chamber to permit the valve seat to return to a normally nondeformed condition and enable the ball to seal the valve opening thus preventing flow of the second fluid, and
   e. controlling the fluid pressure of the chamber at a location remote from the valve.

* * * * *